(12) United States Patent
Wang et al.

(10) Patent No.: US 11,957,333 B1
(45) Date of Patent: Apr. 16, 2024

(54) SUTURE STRUCTURE FOR MEDICAL SURGERY AND PROCESS FOR MAKING THE SAME

(71) Applicant: 2020 (Beijing) Medical Science & Technology Co., Ltd., Beijing (CN)

(72) Inventors: Daiwen Wang, Beijing (CN); Linzhong Wang, Beijing (CN)

(73) Assignee: 2020 (Beijing) Medical Science & Technology Co., Ltd., Beijing (CN)

( * ) Notice: Subject to any disclaimer, the term of this patent is extended or adjusted under 35 U.S.C. 154(b) by 0 days.

(21) Appl. No.: 18/527,466

(22) Filed: Dec. 4, 2023

(30) Foreign Application Priority Data

Jun. 13, 2023 (CN) .......................... 202310693562.8

(51) Int. Cl.
| | |
|---|---|
| *A61B 17/06* | (2006.01) |
| *D02G 3/02* | (2006.01) |
| *D02G 3/34* | (2006.01) |
| *D02G 3/38* | (2006.01) |
| *D02G 3/44* | (2006.01) |
| *A61B 17/00* | (2006.01) |

(52) U.S. Cl.
CPC ......... *A61B 17/06166* (2013.01); *D02G 3/02* (2013.01); *D02G 3/34* (2013.01); *D02G 3/38* (2013.01); *D02G 3/448* (2013.01); *A61B 2017/00526* (2013.01); *A61B 2017/0619* (2013.01); *D10B 2321/021* (2013.01); *D10B 2331/04* (2013.01); *D10B 2509/04* (2013.01)

(58) Field of Classification Search
CPC .... A61B 17/06166; A61B 2017/00663; A61B 2017/06171
See application file for complete search history.

(56) References Cited

U.S. PATENT DOCUMENTS

| | | | | |
|---|---|---|---|---|
| 8,333,788 B2* | 12/2012 | Maiorino | ........... | A61B 17/0401 606/228 |
| 8,663,278 B2* | 3/2014 | Mabuchi | ............ | A61B 17/0401 606/228 |
| 2003/0191497 A1* | 10/2003 | Cope | .................. | A61B 17/0487 606/215 |
| 2004/0260343 A1* | 12/2004 | Leclair | ............... | A61B 17/0401 606/907 |

(Continued)

FOREIGN PATENT DOCUMENTS

| | | |
|---|---|---|
| CN | 213489043 U | 6/2021 |
| CN | 219021334 U | 5/2023 |
| JP | 2006296796 A | 11/2006 |

*Primary Examiner* — Phong Son H Dang

(74) *Attorney, Agent, or Firm* — Cooper Legal Group, LLC

(57) ABSTRACT

The present application provides a suture structure for medical surgery and a process for making the same. The suture structure includes: a thread head core, a winding yarn and a suture connection yarn. In particular, the thread head core is formed by bundling a plurality of thread core yarns; a connection section is provided at a first end of the suture connection yarn; the connection section is attached to the thread head core along a length direction of the thread head core; a second end of the suture connection yarn extends out from the thread head core at the middle of the thread head core; the thread head core and the connection section are wound along the length direction of the thread head core to form a thread rod; and the core yarn, the winding yarn and the suture connection yarn are made of thermoplastic resin fibers.

14 Claims, 2 Drawing Sheets

(56) References Cited

U.S. PATENT DOCUMENTS

2011/0079341 A1* 4/2011 O'Neill .................. B29C 65/56
        156/73.1
2024/0016994 A1* 1/2024 Cherchi ................. A61M 1/84

* cited by examiner

SUTURE STRUCTURE FOR MEDICAL SURGERY AND PROCESS FOR MAKING THE SAME

CROSS-REFERENCE TO RELATED APPLICATION

This application claims the priority and benefit of Chinese patent application No. 202310693562.8, filed on Jun. 13, 2023. The entirety of Chinese patent application No. 202310693562.8 is hereby incorporated by reference herein and made a part of this specification.

TECHNICAL FIELD

The present application relates to the technical field of medical products, and particularly to a suture structure for medical surgery and a process for making the same.

BACKGROUND

During medical surgeries, sutures are mainly used for suturing tissue wounds or surgical incisions, in particular, superficial tissues can be sutured via one single suture, however, in terms of deep tissues, the two sides of tissue wounds or surgical incisions cannot be sutured via one suture. For example, in spine surgery, during a surgery for Lumbar Disc Herniation caused by overflowing or protrusion through wounds of nucleus pulposus in fibrous ring tissues, after a decompression surgery to remove protruding nucleus pulposus is completed, how to suture the tissue wounds or surgical incisions has become a difficult technical challenge to overcome. Since the tissue wounds or surgical incisions facing spinal cord and nerves and there is no operating space, one single suture cannot be introduced from one side of the wound and then threaded out from another side thereof via specialized suture needles. In the related technology, suture is completed through X-close technology, however, which cannot be widely used since metal foreign objects or PEEK materials remained in the body are prone to cause tissue rejection and nerve compression. In related domestic technology, safe suture is completed through methods such as double-needles puncture, driving two different sutures via guide wires and automatic knotting, however, which only can be performed under a few surgical methods such as open or small window opening or the like due to the limitation of the operating space.

SUMMARY

In order to improve the suture convenience for tissue wounds or surgical incisions of deep tissues and reduce the harm to the human body, the present application provides a suture structure for medical surgery and a process for making the same.

In a first aspect, a suture structure for medical surgery according to an embodiment of the present application includes:
  a thread head core, formed by bundling a plurality of thread core yarns;
  a suture connection yarn, wherein a connection section is provided at a first end of the suture connection yarn; the connection section is attached to the thread head core along a length direction of the thread head core; and a second end of the suture connection yarn extends out from the thread head core at the middle of the thread head core;
  a winding yarn, wherein the thread head core and the connection section are wound by the winding yarn along the length direction of the thread head core to form a thread rod; and
  the core yarn, the winding yarn and the suture connection yarn are made of thermoplastic resin fibers.

In the above technical solution, the thread head core is composed of a plurality of the core yarns, and tightly wound with the winding yarns in a straighten state. The thread head core and the winding yarns wound around it are formed a positioning structure having sufficient hardness and support strength. The first end of the suture connection yarn is wound in the thread head core, thereby connecting with the thread head core as a whole. The second end of the suture connection yarn has sufficient flexibility, which is configured for passing through human tissue to suture tissue wounds or surgical incisions to be knotted and fixed. A T-shape structure is formed by the suture connection yarn passing through the sides of the winding yarn and the thread head core.

In a second aspect, a process for making the suture structure for medical surgery according to an embodiment of the present application includes the following steps:
  step S1, fixing a thread head core: arranging a plurality of the thread core yarns side by side to form the thread head core, fixing two ends of the thread head core respectively on a positioning fixture and straightening the thread core yarns;
  step S2, placing a suture connection yarn: fixing a first end of the connection section of the suture connection yarn, wherein, the connection section extends out and is attached to the thread head core along a length direction of the thread head core, and a second end of the suture connection yarn extends out from the thread head core at the middle of the thread head core;
  step S3, winding a winding yarn: tying an end of the winding yarn on the thread head core or the positioning fixture, and spirally tensioning, winding the winding yarn on the thread head core and the connection section, so that the thread head core and the connection section are tied to form a thread rod; and
  step S4, detaching two ends of the thread rod from the positioning fixture; and cutting off redundant.

In the above technical solution, a plurality of the thread core yarns are arranged side by side to form the thread head core, so that the thread head core has sufficient diameters and support hardness. The thread head core is straightened by the positioning fixture, then wound by the winding yarn, which is wrapped on the thread head core composed of the thread core yarns, and the winding yarns remain certain pulling forces when they are wrapped, so that they have certain wrapping forces. Further, the end of the suture structure can be ensured to have sufficient support hardness, which can be stably clamped in inner sides of the surgical target tissues, not fall off after deformation. The suture connection yarn is wound on the thread head core by the winding yarn, such that the suture connection yarn is fixedly connected to the thread head core, in particular, this connection way is stable and there is no knot in the middle of the thread head core, therefore, the thread head core has a uniform diameter.

In summary, the present application has at least one of the following beneficial technical effects:
  1. ends of the suture structure in the present application are of T-shape structure, the suture does not need to around one side to another side of the wound in an inner layer of tissue to be sutured, thereby reducing surgical difficulty;

2. the suture structure in the present application is composed of yarns, which has no negative or exclusive effects to tissue healing;
3. the suture structure in the present application adopts a special knitting process to form a limiting structure at its ends, which is knotted by the yarns integrally, has sufficient support hardness and strength, does not need glue, and is harmless to the human body and healthy.
4. materials, knitting methods, dimensions of the suture structure in the present application are carefully selected, so that the thread head core are not loose and have a compact structure, a uniform diameter, stable connection, and sufficient hardness, tensile strength and support strength; and
5. In terms of technical application, the present application can break the limitations of operating space, meet matching requirements for various minimally invasive surgical methods and instruments, and greatly expand the scope of surgical indications, which can be increased from current 10% to over 90%.

DETAILED DESCRIPTION

The present application will be further described in detail below in combination with FIGS. 1-4.

Embodiment 1

Figure 1:
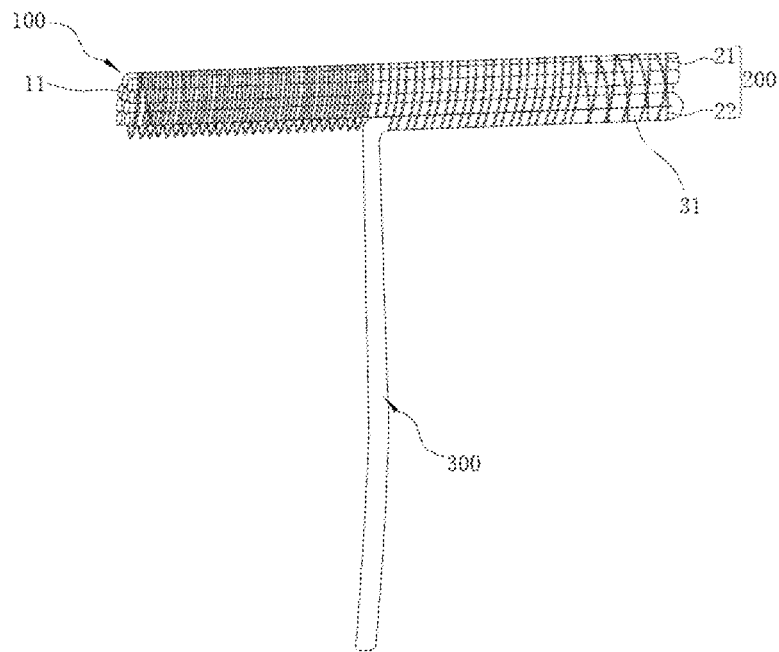
FIG. 1 is a three-dimensional structure diagram of a suture structure according to Embodiment 1.

Referring to FIG. 1, a suture structure for medical surgery includes a thread head core 100, a winding yarn 200 and a suture connection yarn 300. The suture connection yarn 300 includes a first knitting yarn 21 and a second knitting yarn 22 formed by folding a yarn, and the thread head core 100, the first knitting yarn 21 and the second knitting yarn 22 and the suture connection yarn 300 are woven by a plurality of single yarns. The single yarns are strongly polar thermoplastic resin or non-polar thermoplastic resin, which has sufficient strength to ensure that it will not be broken during a winding process, and also has sufficient flexibility, a certain degree of elasticity, and adsorption or viscosity, therefore, the single yarns can be wound tightly during the winding process or loosened when doing other actions after pausing winding, while the single yarns have a certain tightness, so that the loosening yarns can be tensioned again. For example, the single yarn can be made of polyethylene fiber material or polyester fiber material, in which the single yarns made of the polyethylene fiber material have a certain adsorption and an ultra-high tensile strength, and are harmless and provide a comfortable feeling to human after surgery. Numbers of single yarns of the first knitting yarn 21 and the second knitting yarn 22 are less than that of the suture connection yarn 300, or diameters of single yarns of the first knitting yarn 21 and the second knitting yarn 22 are less than that of the suture connection yarn 300, that is, the diameters of the first knitting yarn 21 and the second knitting yarn 22 are less than that of the suture connection yarn 300.

Referring to FIG. 1, a plurality of the thread core yarns 11 are arranged side by side to form a thread head core 100. The plurality of the thread core yarns 11 can be formed by folding a yarn back and forth, finally, a diameter of the formed thread head core 100 is far greater than that of the first knitting yarn 21 and the second knitting yarn 22, a diameter of the suture connection yarn 300 is also greater than that of the first knitting yarn 21 and the second knitting yarn 22, and the diameter of the thread head core 100 is also greater than that of the suture connection yarn 300. The first knitting yarn 21 and the second knitting yarn 22 are spirally wound around the thread head core 100 from a first end to a second end thereof. The first knitting yarn 21 and the second knitting yarn (22) are wound in an opposite winding direction at a starting point of winding on the thread head core 100, and alternately pressed each other on a peripheral surface of the thread head core 100. A locking structure is provided on the thread head core 100 at an ending of winding of the first knitting yarn 21 and the second knitting yarn 22, which is configured to tie thread ends of the first knitting yarn 21 and the second knitting yarn 22. A connection section 31 is provided at a first end of the suture connection yarn 300 along a length direction of the thread head core 100, which is wound around the thread head core 100 by the first knitting yarn 21 and the second knitting yarn 22. A second end of the suture connection yarn 300 extends out at the middle of the thread head core 100 from a gap between the first knitting yarn 21 and the second knitting yarn 22 towards a side of the thread head core 100.

The first knitting yarn 21 and the second knitting yarn 22 are formed after folding a yarn and cutting their connection end, so that the first knitting yarn 21 and the second knitting yarn 22 can be conveniently knotted on the starting point of winding of the thread head core 100, thereby preventing loosening and detachment of the thread ends of the first knitting yarn 21 and the second knitting yarn 22, and rotation of the first knitting yarn 21 and the second knitting yarn 22 when they begin to be wound. The first knitting yarn 21 and the second knitting yarn 22 are wound for 5-8 turns in an opposite direction at the starting point of winding on the thread head core 100, such that they can be pressed by each other to prevent rotation of the first knitting yarn 21 and the second knitting yarn 22 around the thread head core 100 during the winding process, thereby facilitating production and a possibility of loosening their thread ends after cutting the connection end of the first knitting yarn 21 and the second knitting yarn 22. The first knitting yarn 21 and the second knitting yarn 22 are wound along a same direction until at the ending of winding of the first knitting yarn 21 and the second knitting yarn 22 on the thread head core 100. The first knitting yarn 21 and the second knitting yarn 22 are wound along the same direction for easy operation, thereby improving a processing efficiency of the suture structure. Certainly, the first knitting yarn 21 and the second knitting yarn 22 are also wound in opposite directions until at the ending of winding of the first knitting yarn 21 and the second knitting yarn 22 on the thread head core 100.

The implementation principle is that: the thread head core 100 is composed of the plurality of thread core yarns 11, and tightly wound with the first knitting yarn 21 and the second knitting yarn 22 in a straighten state. The thread head core 100, and the first knitting yarn 21 and the second knitting yarn 22 wound on the thread head core 100 are formed a positioning structure having sufficient hardness and support strength. The first end of the suture connection yarn 300 is wound in the thread head core 100, thereby connecting with the thread head core 100 as a whole. The second end of the suture connection yarn 300 has sufficient flexibility, which is configured for passing through suture wounds of human tissues and knotting to be fixed. The suture connection yarn 300 passing through the sides of the first knitting yarn 21 and the second knitting yarn 22 and the thread head core 100 are formed to a T-shape structure, in which the thread head core 100, the attached first knitting yarn 21 and second knitting yarn 22, and the connection section 31 of the suture connection yarn 300 are defined as one horizontal of the T-shape structure, which has certain hardness and supporting and positioning effects in a suture surgery as a rod body, thereby preventing detachment of the suture structure from sutured tissues. A part of the suture connection yarn 300 which is not bound on the thread head core 100 is defined as one vertical of the T-type structure, which has certain flexibility and pulls the suture wound as a connection wire at the outer side of the sutured tissues after tied with the suture structure.

Taking suturing the wounds on fibrous rings as an example, specifically, when the suture structure is used, an end of the suture structure having the thread head core 100 is placed in a puncture needle, and the puncture needle is inserted from the fibrous ring tissue on a first side of the wound into the inside thereof, and an end of the thread head core 100 is pushed out of the puncture needle via a push rod thereof, finally, the puncture needle is removed, such that the end of the thread head core 100 can be removed into the fibrous ring to be sutured via the puncture needle, and the end of the suture structure cannot be detached from the inner side of the fibrous rings due to the T-shape structure of the thread head core 100. For the same reason, another suture structure is placed into a second side of the wound of the fibrous ring, the two suture structures are knotted at outside of the fibrous ring, so that the tissues at the two sides of the wound can be attached and fixed.

In the present application, the plurality of the thread core yarns 11 are arranged side by side to form the thread head core 100. The suture connection yarn 300 is connected to the thread head core 100 by adopting the above suture structure, which is capable of ensuring that both ends of the thread head core 100 are not loose and have the compact structure, and the thread head core 100 has the uniform diameter and the stable connection with the suture connection yarn 300. While the produced thread head core 100 has sufficient hardness and support strength, so that the suture connection yarn 300 has sufficient connection strength besides meeting a flexibility requirement.

It should be illustrated that, in the present application, the first knitting yarn 21 and the second knitting yarn 22 are tightly wrapped around the thread head core 100. In FIG. 1, the gap between the first knitting yarn 21, the second knitting yarn 22 and the thread head core 100 is configured for illustration, not the specific production sample.

Embodiment 2

Figure 2:
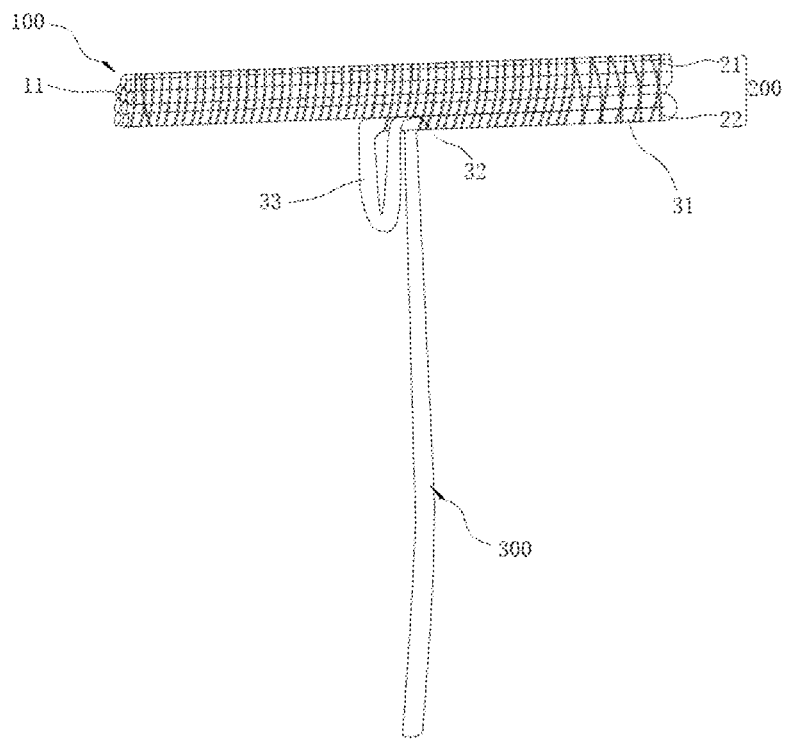
FIG. 2 is a three-dimensional structure diagram of a suture structure according to Embodiment 2.

Referring to FIG. 2, this embodiment is almost same as Embodiment 1 expects that the suture connection yarn 300 is provided with a shrinkable loop 33 with a slipknot at the middle of the thread head core 100 in this embodiment. During the surgery, the suture structure with the shrinkable loop 33 is cooperated with the suture structure without the shrinkable loop 33, the suture connection yarn 300 of the suture structure without the shrinkable loop 33 passes through the shrinkable loop 33 of another suture structure, then pulling the two suture connection yarns 300 can realize self-locking knotting and tightening.

Embodiment 3

Figure 3:
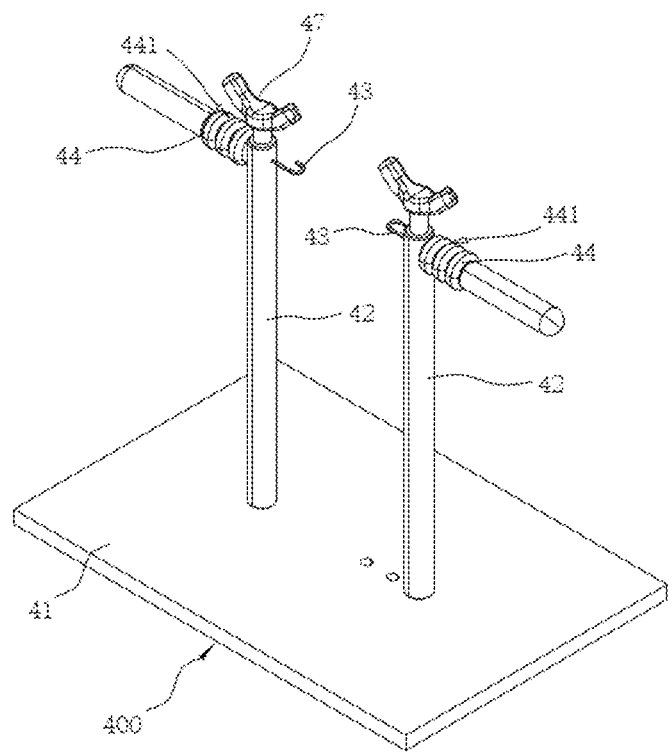
FIG. 3 is a three-dimensional structure diagram of a positioning fixture according to Embodiment 3.

A process for making the suture structure of the Embodiment 1 is provided in this embodiment, and a positioning fixture 400 is used in the process, referred to FIG. 3. The positioning fixture 400 includes a support base plate 41 and two positioning columns 42 fixedly provided on the support base plate 41 with space apart from each other, a transverse wire hook 43 is provided on each of opposite sides of the two positioning columns 42, and the transverse wire hooks 43 of the two positioning columns 42 are arranged opposite to each other. A transverse rubber block 44 is provided on each of back sides, relative to the opposite sides, of the two positioning columns 42, and a clamping groove 441 is provided on each of the transverse rubber blocks 44. The top ends of the two positioning columns 42 are provided with butterfly bolts 47.

A process for making the suture structure of this embodiment includes the following steps:

step S0, a thread head core 100, a winding yarn 200 and a suture connection yarn 300 are de-staticized; for example, the thread head core 100, the winding yarn 200 and the suture connection yarn 300 may be de-staticized by blowing an ionizing airflow to them with an ionizing blower;

step S1, fixing a thread head core 100: a plurality of the thread core yarns 11 are arranged side by side to form the thread head core 100, two ends of the thread head core 100 are relatively and fixedly connected on the positioning fixture 400 to tension the thread core yarns 11. The plurality of the thread core yarns 11 can be many single yarns whose two ends are relatively and fixedly connected on the two positioning columns 42, and also can be formed by winding one or more yarns on the two opposite wire hooks 43 back and forth. For example, after a yarn is folded, one end thereof is hooked on a wire hook 43 of one positioning column 42, and two yarns formed on another end thereof are wound on the two wire hooks 43 back and forth. When the required diameter of the yarn is obtained, two ends of the yarn are clamped in the clamping grooves 441 of the rubber blocks 44, then the thread heads are clamped and fixed due to the deformable force of the rubber blocks 44, thereby facilitating conveniently and quickly fixing the thread core yarns 11 to form the thread head core 100 and adjust its diameter;

step S2, placing a suture connection yarn 300: a first end of the suture connection yarn 300 is fixed, and a second end thereof extends to the middle of the thread head core 100 along its linear direction, and is attached on the thread head core 100;

step S3, winding a first knitting yarn 21 and a second knitting yarn 22: a yarn is tied on the thread head core 100 to form two folded parts, and the two folded parts of the yarn are defined as a first knitting yarn 21 and a second knitting yarn 22, respectively. The first knitting yarn 21 is spirally wound clockwise around on the thread head core 100, while the second knitting yarn 22 is spirally wound counterclockwise around on the thread head core 100, and the first knitting yarn 21 and the second knitting yarn 22 are alternatively pressed on each other on a peripheral surface of the thread head core 100. When the first knitting yarn 21 and the second knitting yarn 22 are spirally wound at an ending point of the thread head core 100, the suture connection yarn 300 is folded at a starting fixing end to be fixed. After the first knitting yarn 21 and the second knitting yarn 22 are spirally wound in opposite directions to the middle of the thread head core 100, the suture connection yarn 300 extends outside the first knitting yarn (21) and the second knitting yarn (22) from a gap between the first knitting yarn 21 and the second knitting yarn 22. The first knitting yarn 21 and the second knitting yarn 22 are continued to be spirally wound at a starting point of the thread head core, it needs to be determined whether to continue spirally winding the first knitting yarn 21 and the second knitting yarn 22 on one side of the middle of the thread head core 100 based on diameters on two sides of the middle of the thread head core 100, and when the diameters of the two sides of the middle of the thread head core 100 are equal or similar, the thread ends of the first knitting yarn 21 and the second knitting yarn 22 are tied together. When the first knitting yarn 21 and the second knitting yarn 22 are wound to the ending point to be knotted, firstly, a loop of the first knitting yarn 21 is leaved and extends the first knitting yarn 21 in a straight along the length direction of the thread head core 100, the loop can temporarily be sleeved on the butterfly bolt 47 to prevent loosening; secondly, the second knitting yarn 22 is continued to be wound on the thread head core 100 and the first knitting yarn 21 for 1-1.5 mm to form a wrapping layer such that the second knitting yarn 22 returns and passes through the loop; thirdly, the first knitting yarn 21 is tensioned such that the loop shrinks, and the second knitting yarn 22 is pulled into range of the wrapping layer such that the first knitting yarn 21 and the second knitting yarn 22 are tightly tied together. Therefore, the first knitting yarn 21 and the second knitting yarn 22 can be easily tied together, there is no large knot protrusion on the thread head core 100, and the wrapped yarn will not loosen after cutting the first knitting yarn 21 and the second knitting yarn 22 short. The suture connection yarn 300 passing through the sides of the first knitting yarn 21 and the second knitting yarn 22 and the thread head core 100 are formed to a T-shape structure, in which the thread head core 100, the attached first knitting yarn 21 and second knitting yarn 22, and the connection section 31 of the suture connection yarn 300 are defined as one horizontal of the T-type structure, which has certain hardness and supporting and positioning effects in a suture surgery as a rod body, thereby preventing detachment of the suture structure from sutured tissues. A part of the suture connection yarn 300 which is not bound on the thread head core 100 is defined as one vertical of the T-type structure, which has certain flexibility and pulls the tissue wounds or surgical incisions as a connection wire at the outer side of the sutured tissues after knotted with the suture structure; step S4, two ends of the thread head core 100 are detached from the positioning fixture 400; redundant yarns are cut depending on the required length and relative structures having tying thread end functions at two ends of the first knitting yarn 21 and second knitting yarn 22 should be remained during a cutting process.

In the embodiment, a diameter of the suture connection yarn 300 is greater than that of the first knitting yarn 21 and the second knitting yarn 22. The end of the suture connection yarn 300 is tied at one end of the thread head core 100, and a specific location is determined based on a length of a limiting structure at head required by the suture yarn. The first knitting yarn 21 and the second knitting yarn 22 are mainly configured for tying the thread head core 100 to form a rod body with certain hardness, and connecting an end of the suture connection yarn 300 on the thread head core 100 through winding and tying. Therefore, the first knitting yarn 21 and the second knitting yarn 22 can adopt thin yarns, so that first knitting yarn 21 and the second knitting yarn 22 have small diameters, and there are no large protrusions on the thread head core 100 when tying knots. The suture connection yarn 300 is configured for pulling the tissues at two sides of the wound and should bear a certain pulling force, which is used thick yarns to ensure its connection strengthen. Therefore, large protrusions cannot be leaved on the thread head core 100 by the suture connection yarn 300.

Further, in the above step S3, a yarn is folded, and tied at an end of the thread head core 100 composed of a plurality of the thread core yarns. The first knitting yarn 21 and the second knitting yarn 22 are spirally wound on the thread head core 100 in opposite directions. After the first knitting yarn 21 and the second knitting yarn 22 are wound for 5-8 turns, they are wound in a same direction at the ending point of the first knitting yarn 21 and the second knitting yarn 22. The first knitting yarn 21 and the second knitting yarn 22 are wound for 5-8 turns in opposite directions, which can effectively prevent rotation during their winding process and loosening of the thread ends. At the same time, the first knitting yarn 21 and the second knitting yarn 22 are conveniently wound in a same direction, thereby improving processing efficiency of the suture structure.

An implementation principle is: a plurality of the thread core yarns 11 are arranged side by side to form the thread head core 100, so that the thread head core 100 has sufficient diameter and support hardness. The thread head core 100 is straightened by the positioning fixture 400, and wound by the first knitting yarn 21 and the second knitting yarn 22. The thread head core 100 composed of the thread core yarns 11 is wrapped by the first knitting yarn 21 and the second knitting yarn 22, and the first knitting yarn 21 and the second knitting yarn 22 remain certain pulling forces when they are wrapped, so that they have certain wrapping forces. Further, the end of the suture structure can be ensured to have sufficient support hardness, which can be stably clamped in an inner side of the surgical target tissues, not fall off after deformation. The suture connection yarn 300 is wound on the thread head core 100 by the first knitting yarn 21 and the second knitting yarn 22, such that the suture connection yarn 300 is fixedly connected to the thread head core 100, in particular, this connection way is stable and there is no knot in the middle of the thread head core 100, therefore, the thread head core 100 has the uniform diameter.

Embodiment 4

This embodiment is almost same as Embodiment 3 except that, in this embodiment, an end of a connection section 31 of a suture connection yarn 300 can be directly fixedly connected on a positioning fixture 400, that is, both ends of the suture connection yarn 300 are fixedly connected on the positioning fixture 400. The two ends of the suture connection yarn 300 are wound on wire hooks 43 of two positioning columns 42, or the suture connection yarn 300 can be fixed after being wound for 2-3 turns in clamping grooves 441 of the rubber blocks 44, thereby attaching on the thread head core 100. The suture connection yarn 300 has a same length direction with the thread head core 100. When the first knitting yarn 21 and the second knitting yarn 22 are wound to the middle of the thread head core 100, an end of the suture connection yarn 300 departing from the connection section 31 are loosened to detach the suture connection yarn 300 from the thread head core 100, and the first knitting yarn 21 and the second knitting yarn 22 are continued to be wound on the thread head core 100 until its end, then the suture connection yarn 300 passes through the first knitting yarn 21 and the second knitting yarn 22, thereby finally forming a T-shape structure.

Embodiment 5

Referring to FIG. 2, this embodiment is almost same as Embodiment 3 or 4 expect that, in step S3 of this embodiment, when the first knitting yarn 21 and the second knitting yarn 22 are spirally wound in opposite directions to the middle of the thread head core 100, the suture connection yarn 300 extends outside the first knitting yarn 21 and the second knitting yarn 22 from a gap between the first knitting yarn 21 and the second knitting yarn 22. After the first knitting yarn 21 and the second knitting yarn 22 is continued to be spirally wound for 1-3 turns, the suture connection yarn 300 attaches to the thread head core 100 again. Then, the first knitting yarn 21 and the second knitting yarn 22 are continued to be spirally wound for 1-3 turns to wrap the suture connection yarn 300 on the thread head core 100. A yarn sleeve 32 is formed at the outer sides of the first knitting yarn 21 and the second knitting yarn 22 by the suture connection yarn 300, and the suture connection yarn 300 extends outside of the first knitting yarn 21 and the second knitting yarn 22, and is folded back to pass through the yarn sleeve 32 to form a shrinkable loop 33, thereby finally forming a suture structure with the shrinkable loop 33 in the Embodiment 2.

During each suture surgery, the suture structure with the shrinkable loop 33 and the suture structure without the shrinkable loop 33 are formed a group of suture wires to combined use, the suture connection yarn 300 in the suture structure without the shrinkable loop 33 passes through the shrinkable loop 33 of another suture structure, then pulling the two shrinkable loops 33 can realize self-locking knotting and ensure tight tying of the two yarns, this is very convenient.

Embodiment 6

Figure 4:
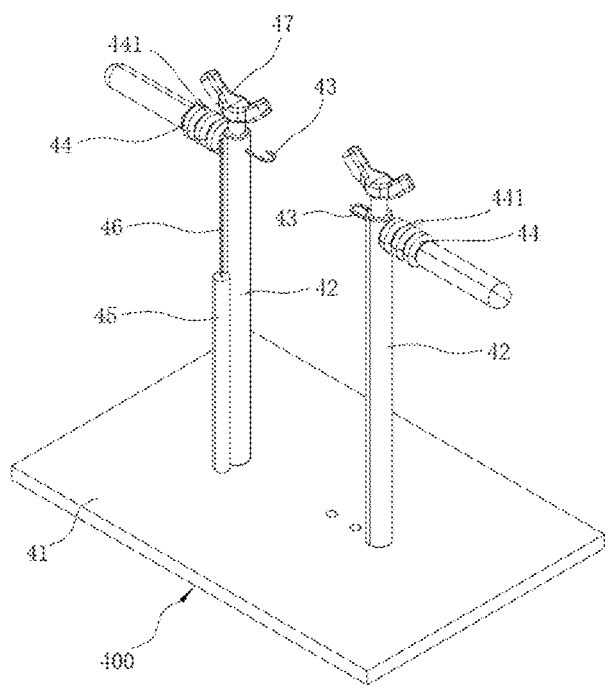
FIG. 4 is a three-dimensional structure diagram of a positioning fixture according to Embodiment 6.

Referring to FIG. 4, this embodiment is almost same as one of Embodiments 3-5 expect that, in this embodiment, a mounting column 45 is provided on a support base plate 41 at a side of one positioning column 42, and an alloy wire column 46 is provided on the top end of the mounting column 45. In step S3, when the first knitting yarn 21 are wound and tied with the second knitting yarn 22, a loop of the first knitting yarn 21 is sleeved on the alloy wire column 46. After the second knitting yarn 22 passes through the loop, the first knitting yarn 21 is pulled such that the loop detaches from the alloy wire column 46. Alternatively, when the shrinkable loop 33 of the Embodiment 5 is wound, the yarn sleeve 32 formed by the suture connection yarn 300 is sleeved on the alloy wire column 46. After the suture connection yarn 300 passes through the yarn sleeve 32, the yarn sleeve 32 is detached from the alloy wire column 46. The alloy wire column 46 can assist in pulling the loop or yarn sleeve, effectively avoiding loosening, shrinkage, and other phenomena.

The alloy wire column 46 not only has sufficient support strengthen, but also certain hardness. After the loop or yarn sleeve is sleeved on the alloy wire column 46, the alloy wire column 46 is able to be bent to extend to the thread head core 100 after applied an external force, therefore, the loop or yarn sleeve 32 can be adjusted, and facilitate detaching from the alloy wire column 46, which is convenient.

The above are the preferred embodiments of the present application, which are not intended to limit the protection scope of the present application, in particular, the same components are represented by the same reference mark. Therefore, all equivalent changes made according to the structure, shape and principle of the present application should be covered within the protection scope of the present application.

LIST OF REFERENCE SIGNS 100. thread head core;
11. thread core yarn;
200. winding yarn;
21. first knitting yarn;
22. first knitting yarn;
300. suture connection yarn;
31. connection section;
32. yarn sleeve;
33. shrinkable loop;
400. positioning fixture;
41. support base plate;
42. positioning column;
43. wire hook;
44. rubber block;
45. mounting column;
46. alloy wire column;
47. butterfly bolt.

What is claimed is:

1. A suture structure for medical surgery, comprising:
a thread head core, formed by bundling a plurality of thread core yarns;
a suture connection yarn, wherein a connection section is provided at a first end of the suture connection yarn; the connection section is attached to the thread head core along a length direction of the thread head core; and a second end of the suture connection yarn extends out from the thread head core at a middle of the thread head core wherein the suture connection yarn forms a shrinkable loop in a form of a slipknot at the middle of the thread head core; and
a winding yarn, wherein the thread head core and the connection section are wound by the winding yarn along the length direction of the thread head core to form a thread rod;
wherein the plurality of thread core yarns, the winding yarn and the suture connection yarn are made of thermoplastic resin fibers.

2. The suture structure for medical surgery according to claim 1, wherein the winding yarn comprises a first knitting yarn and a second knitting yarn; the first knitting yarn and the second knitting yarn are spirally wound around the thread head core from a first end to a second end of the thread head core, or the first knitting yarn and the second knitting yarn are spirally wound around the thread head core from the middle of the thread head core to one of the first end or the second end of the thread head core; the first knitting yarn and the second knitting yarn are wound in opposite winding directions at a starting point of winding on the thread head core, and the first knitting yarn and the second knitting yarn alternately press each other on a peripheral surface of the thread head core; and the first knitting yarn and the second knitting yarn are knotted at an ending of the winding on the thread head core for locking thread ends of the first knitting yarn and the second knitting yarn.

3. The suture structure for medical surgery according to claim 1, wherein the plurality of thread core yarns, the winding yarn and the suture connection yarn are made of polyethylene fiber material or polyester fiber material.

4. A process for making the suture structure for medical surgery according to claim 1, comprising:
step S1, fixing the thread head core by arranging the plurality of thread core yarns side by side to form the thread head core, fixing two ends of the thread head core respectively on a positioning fixture and straightening the plurality of thread core yarns;
step S2, placing the suture connection yarn by fixing a first end of the connection section of the suture connection yarn, wherein the connection section extends and is attached to the thread head core along the length direction of the thread head core, and the second end of the suture connection yarn extends out from the thread head core at the middle of the thread head core;
step S3, winding the winding yarn by tying an end of the winding yarn on the thread head core or the positioning fixture, and spirally tensioning, and winding the winding yarn on the thread head core and the connection section, so that the thread head core and the connection section are tied to form the thread rod; and
step S4, detaching two ends of the thread rod from the positioning fixture; and cutting off redundant yarns;
wherein the positioning fixture comprises a support base plate and two positioning columns fixedly provided on the support base plate with space apart from each other, and a transverse wire hook is provided on each of opposite sides on a middle or a top of the two positioning columns, a transverse rubber block is provided on each of back sides, relative to the opposite sides, of the two positioning columns, a clamping groove is provided on each of the transverse rubber blocks, and the transverse wire hooks of the two positioning columns are arranged opposite to each other; a mounting column is provided on the support base plate close to one of the two positioning columns, and an alloy wire column is provided on a top end of the mounting column; the step S1 further comprises: winding one or more yarns on the transverse wire hooks back and forth to form the plurality of the thread core yarns; and the step S2 further comprises: winding the suture connection yarn for a plurality of turns in the clamping grooves of the transverse rubber blocks to secure the suture connection yarn.

5. The process for making the suture structure for medical surgery according to claim 4, wherein the winding yarn comprises a first knitting yarn and a second knitting yarn; the step S3 further comprises: tying a first end of the first knitting yarn and a first end of the second knitting yarn on the thread head core or the positioning fixture, spirally winding a second end of the first knitting yarn clockwise on the thread head core and the connection section, and spirally winding a second end of the second knitting yarn counterclockwise on the thread head core and the connection section; alternately pressing the first knitting yarn and the second knitting yarn with each other to be wound for a number of turns on a peripheral surface of the thread head core and the connection section; spirally winding the first knitting yarn and the second knitting yarn on the thread head core and the connection section in a same direction or opposite directions; after the first knitting yarn and the second knitting yarn are spirally wound to an end of the thread head core, folding the connection section back to a starting fixing end to be fixed; after the first knitting yarn and the second knitting yarn are wound in the opposite directions on the thread head core and a turn-back section of the connection section to the middle of the thread head core, extending the first end of the suture connection yarn outside the first knitting yarn and the second knitting yarn from a gap between the first knitting yarn and the second knitting yarn; and when the first knitting yarn and the second knitting yarn are wound to an ending position, tying the first knitting yarn and the second knitting yarn together.

6. The process for making the suture structure for medical surgery according to claim 5, wherein the step S3 further comprises: after the first knitting yarn and the second knitting yarn are spirally wound from the middle to a starting point of the thread head core, determining whether to continue winding the first knitting yarn and the second knitting yarn on one side of the middle of the thread head core based on diameters of two sides of the middle of the thread head core, and when the diameters of the two sides of the middle of the thread head core are equal, spirally winding the first knitting yarn and the second knitting yarn to an ending point of the thread head core, and tying the first knitting yarn and the second knitting yarn together.

7. The process for making the suture structure for medical surgery according to claim 5, wherein in the step S2, a diameter of the suture connection yarn is greater than a diameter of the first knitting yarn and a diameter of the second knitting yarn; and an end of the suture connection yarn is fixedly connected to the positioning fixture or tied on the end of the thread head core.

8. The process for making the suture structure for medical surgery according to claim 5, wherein the step S3 further comprises: folding a yarn to form two folded parts and tying the folded yarn to the end of the thread head core consisting of the plurality of thread core yarns, wherein the two folded parts of the folded yarn are defined as the first knitting yarn and the second knitting yarn respectively; alternatively spirally winding the first knitting yarn and the second knitting yarn on the thread head core in the opposite directions; and after the first knitting yarn and the second knitting yarn are wound for a second plurality of turns, winding the first knitting yarn and the second knitting yarn in a same direction to an ending point where winding of the first knitting yarn and the second knitting yarn ends.

9. The process for making the suture structure for medical surgery according to claim 4, wherein the step S3 further comprises: when a first knitting yarn and a second knitting yarn are wound to an ending point, leaving a loop of the first knitting yarn and extending the first knitting yarn in a straight along the length direction of the thread head core; continuing to wind the second knitting yarn on the thread head core and the first knitting yarn for 1-1.5 mm to form a wrapping layer such that the second knitting yarn returns and passes through the loop; tensioning the first knitting yarn such that the loop shrinks, and pulling the second knitting yarn into range of the wrapping layer such that the first knitting yarn and the second knitting yarn are tied together.

10. The process for making the suture structure for medical surgery according to claim 9, wherein the step S3 further comprises: in winding and tying of the first knitting yarn and the second knitting yarn, sleeving the loop of the first knitting yarn on the alloy wire column; and after the second knitting yarn passes through the loop, pulling the first knitting yarn such that the loop detaches from the alloy wire column.

11. The process for making the suture structure for medical surgery according to claim 10, wherein the alloy wire column is configured to be bent to extend to the thread head core.

12. The process for making the suture structure for medical surgery according to claim 4, wherein the step S3 further comprises: when a first knitting yarn and a second knitting yarn are spirally wound in opposite directions to the middle of the thread head core, extending the suture connection yarn outside the first knitting yarn and the second knitting yarn from a gap between the first knitting yarn and the second knitting yarn; continuing to spirally wind the first knitting yarn and the second knitting yarn for a second plurality of turns, such that the suture connection yarn is attached to the thread head core again; continuing to spirally wind the first knitting yarn and the second knitting yarn for a third plurality of turns to wrap the suture connection yarn on the thread head core, such that the suture connection yarn forms a yarn sleeve outside the first knitting yarn and the second knitting yarn; and extending the suture connection yarn outside the first knitting yarn and the second knitting yarn again, such that the suture connection yarn is folded back to pass through the yarn sleeve to form a shrinkable loop.

13. The process for making the suture structure for medical surgery according to claim 12, wherein the step S3 further comprises: when the shrinkable loop is wound, sleeving the yarn sleeve formed by the suture connection yarn on the alloy wire column; and after the suture connection yarn passes through the yarn sleeve, detaching the yarn sleeve from the alloy wire column.

14. The process for making the suture structure for medical surgery claim 4, wherein, before step S1, the process further comprises: de-staticizing the thread head core, the winding yarn and the suture connection yarn.

* * * * *